United States Patent [19]

Huhn et al.

[11] 4,304,717
[45] * Dec. 8, 1981

[54] PROCESS FOR THE PREPARATION OF REACTIVE PENICILLANIC ACID AND CEPHALOSPORANIC ACID DERIVATIVES

[75] Inventors: Magda Huhn; Gabor Szabo; Gabor Resofszki; Eva Somfai, all of Budapest, Hungary

[73] Assignee: Chinoin Gyogyszer es Vegyeszeti Termekek Gyara Rt, Budapest, Hungary

[*] Notice: The portion of the term of this patent subsequent to Oct. 16, 1996, has been disclaimed.

[21] Appl. No.: 36,756

[22] Filed: May 7, 1979

Related U.S. Application Data

[63] Continuation of Ser. No. 812,735, Jul. 5, 1977, Pat. No. 4,171,303, which is a continuation-in-part of Ser. No. 598,692, Jul. 24, 1975, abandoned.

[30] Foreign Application Priority Data

Jul. 30, 1974 [HU] Hungary .............................. CI 1499

[51] Int. Cl.$^3$ .................. C07D 499/12; C07D 501/06
[52] U.S. Cl. .................................. 260/239.1; 544/22; 544/28; 544/30
[58] Field of Search .................. 260/239.1; 544/22, 28

[56] References Cited

U.S. PATENT DOCUMENTS 4,171,303 10/1979 Huhn et al. ...................... 260/239.1

FOREIGN PATENT DOCUMENTS 1004670 9/1965 United Kingdom ............. 260/239.1

Primary Examiner—Natalie Trousof
Assistant Examiner—Vera C. Clarke
Attorney, Agent, or Firm—Karl F. Ross

[57] ABSTRACT

This invention relates to a process for the preparation of acid amides having the formula (I) or their salts

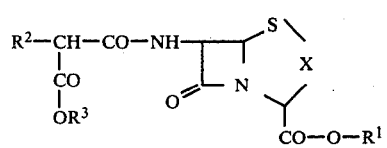

(I)

wherein
$R^1$ is hydrogen or an easily removable ester-forming or salt-forming group, preferably a trialkylamine, trialkylsilyl, trichloroethyl, acetoxymethyl, phenacyl, substituted phenacyl, substituted phenyl or benzyl group, $R^2$ is hydrogen, alkyl group, alkenyl group, alkyl group having an aryl or heterocyclic (preferably furyl or thienyl) - substituent, an aryl group having an alkyl substituent (preferably xylyl), or an aryl, aralkyl or heterocyclic group (preferably a phenyl, thienyl, or furyl group) which can have one or more substituents, $R^3$ is hydrogen, or substituted or unsubstituted aryl, alkyl, cycloalkyl or aralkyl group, and X is a group of one of the formulae

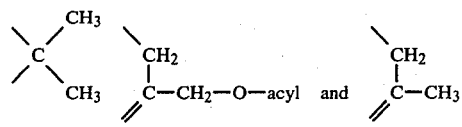

according to the invention an amine of the formula (II),

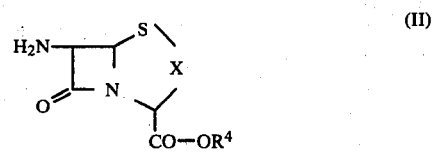

(II)

wherein $R^4$ is an easily removable ester-forming group, preferably a trialkylamino, trialkylsilyl, trichloroethyl, acetoxymethyl, phenacyl, substituted phenacyl, substituted phenyl or benzyl group, or a salt formed preferably with an alkali metal or a trialkylamine, is acylated with an ester of the formula (III),

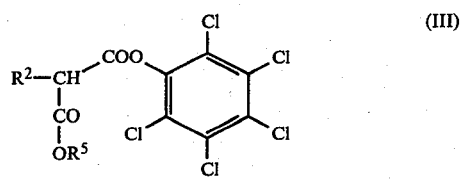

(III)

wherein $R^5$ is a substituted or unsubstituted aryl, alkyl, cycloalkyl or aralkyl group, and, if desired, substituents $R^4$ and/or $R^5$ of the obtained product can be split off, and/or, if desired, the obtained product is converted into its salt or a salt is converted into the free acid.

7 Claims, No Drawings

PROCESS FOR THE PREPARATION OF REACTIVE PENICILLANIC ACID AND CEPHALOSPORANIC ACID DERIVATIVES

CROSS REFERENCE TO RELATED APPLICATION

This application is a continuation of Ser. No. 812,735 filed July 5, 1977, now U.S. Pat. No. 4,171,303; which is a continuation-in-part of Ser. No. 598,692, filed July 24, 1975, now abandoned.

This invention relates to a process for the preparation of acid amides having the formula (I) or their salts.

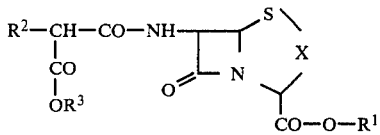

wherein
$R^1$ is hydrogen or an easily removable ester-forming or salt-forming group, preferably a trialkylamine, trialkylsilyl, trichloroethyl, acetoxymethyl, phenacyl, substituted phenacyl, substituted phenyl or benzyl, $R^2$ is hydrogen, alkyl, alkenyl, alkyl having an aryl or heterocyclic (preferably furyl or thienyl)-substituent, an aryl group having an alkyl substituent (preferably xylyl), or an aryl, aralkyl or heterocyclic group (preferably a phenyl, thienyl or furyl group which can have one or more substituents, $R^3$ is hydrogen, or unsubstituted or unsubstituted aryl, alkyl, cycloalkyl or aralkyl group, and X is a group of one of the formulae

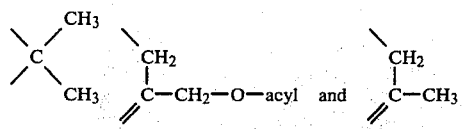

where $R^1$ is trialkylamine or trialkylsilyl the alkyl group contains from 1 to 6 carbon atoms. Where $R^1$ is substituted phenacyl, the substituents may be one or more of nitro, halogen, $C_1$ to $C_6$ alkyl, $C_1$ to $C_6$ alkoxy or hydroxy. Where $R^1$ is substituted phenyl, the substituents may be one or more of nitro, halogen, $C_1$ to $C_6$ alkyl, $C_1$ to $C_6$ alkoxy, or hydroxy.

Where $R^2$ is alkyl the alkyl group contains from 1 to 6 carbon atoms. Where $R^2$ is alkenyl the alkenyl group contains from 1 to 6 carbon atoms. Where $R^2$ is aryl, the aryl is preferably, phenyl, 1-naphthyl 2-naphthyl or 5-indanyl. Where $R^2$ is heterocyclic the heterocyclic group is preferably furyl or thienyl. Where $R^2$ is substituted aryl, the aryl group is defined above and the substituents may be one or more $C_1$ to $C_6$ alkyl, $C_1$ to $C_6$ alkoxy, nitro, halogen, or hydroxy. A preferred substituted aryl is xylyl. Where $R^2$ is a substituted heterocyclic group the heterocyclic group is as defined above and the substituents may be one or more $C_1$ to $C_6$ alkyl, $C_1$ to $C_6$ alkoxy, nitro, halogen or hydroxy groups. Where $R^2$ is aralkyl, the preferred aralkyl is benzyl and where $R^2$ is substituted aralkyl the substituents include one or more $C_1$ to $C_6$ alkyl, $C_1$ to $C_6$ alkoxy, nitro, halo- gen or hydroxy. Unless otherwise stated $R^5$ and $R^6$ have similarly limited meanings.

Where $R^3$ is aryl, substituted aryl, aralkyl or substituted aralkyl, these groups are the same as those defined in $R^2$. Where $R^3$ is alkyl the alkyl contains from 1 to 6 carbon atoms and where $R^3$ is substituted alkyl, the substituents are one or more halo, hydroxy, or $C_1$ to $C_6$ alkoxy groups. Where $R^3$ is cycloalkyl, the cycloalkyl contains from 4 to 7 carbon atoms. Where $R^3$ is substituted cycloalkyl, the substituents include one or more $C_1$ to $C_6$ alkyl, $C_1$ to $C_6$ alkoxy, hydroxy or halogen.

Where X is acyl, the acyl is preferably a residue of a $C_1$ to $C_6$ aliphatic carboxylic acid.

According to the invention an amine of the formula (II),

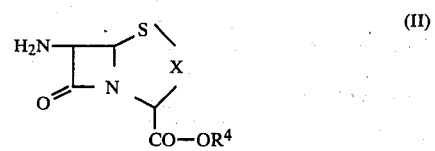

wherein $R^4$ is an easily removable ester-forming group, preferably a trialkylamino, trialkylsilyl, trichloroethyl, acetoxymethyl, phenacyl, substituted phenacyl, substituted phenyl or benzyl group, or a salt formed preferably with an alkali metal or a trialkylamine, is acylated with an ester of the formula (III),

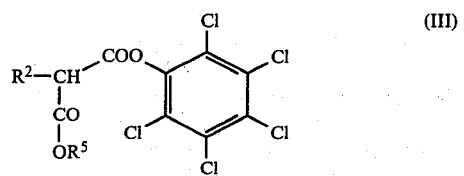

wherein $R^5$ is a substituted or unsubstituted aryl, alkyl, cycloalkyl or aralkyl, and, if desired, substituents $R^4$ and/or $R^5$ of the obtained product can be split off, and/or, if desired, the obtained product is converted into its salt or a salt is converted into the free acid.

The penicillanic acid and cephalosporanic acid derivatives prepared according to the invention, containing a carboxy group in the α-position of the side chain, possess valuable antibacterial effects against both Gram-negative and Gram-positive microorganisms, and can be used with good results in the human or veterinary therapy.

Those compounds of the formula (I), wherein $R^2$ is for alkyl are novel. The preferred compounds are A compound of the formula Ia or a pharmaceutically acceptable salt thereof

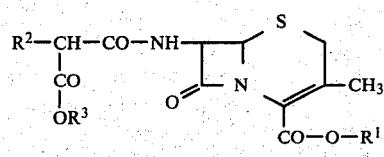

wherein
$R^1$ is hydrogen, trichloroethyl, acetoxymethyl, phenacyl, p-nitrophenacyl or benzyl'
$R^2$ is hydrogen, propyl, phenyl, 3-thienyl, p-chlorophenyl, or o-bromophenyl; and R³ is hydrogen, phenyl, 5-indanyl, benzyl or pentachlorophenyl.

The preferred ultimate species are:

7-(α-Phenoxycarbonyl-phenylacetamido)-3-methyl-ceph-3-em-4-carboxylic acid, 7-(α-[5-Indanyloxycarbonyl]-phenylacetamido)-3-methyl-ceph-3-em-4-carboxylic acid, 7-(α-Phenoxycarbonyl-phenylacetamido)-3-methyl-ceph-3-em-4-carboxylic acid triethylammonium salt, 7-(α-Carboxy-3-thienyl-acetamido)-3-methyl-ceph-3-em-4-carboxylic acid, 7-(α-[5-Indanyloxycarbonyl]-phenylacetamido)-3-methyl-ceph-3-em-4-carboxylic acid trichloroethyl ester, 7-(α-Benzyloxycarbonyl-phenylacetamido)-3-methyl-ceph-3-em-4-carboxylic acid, 7-(α-Phenoxycarbonyl-phenylacetamido)-3-methyl-ceph-3-em-4-carboxylic acid trichloroethyl ester, 7-(α-Carboxy-phenylacetamido)-3-methyl-ceph-3-em-4-carboxylic acid, 7-(α-Pentachlorophenoxycarbonyl-phenylacetamido)-3-methyl-ceph-3-em-4-carboxylic acid trichloroethyl ester, 7-(α-Benzyloxycarbonyl-phenylacetamido)-3-methyl-ceph-3-em-4-carboxylic acid trichloroethyl ester, 7-(α-Pentachlorophenoxycarbonyl-phenylacetamido)-3-methyl-ceph-3-em-4-carboxylic acid p-nitro-phenacylester, 7-(α-Phenoxycarbonyl-phenylacetamido)-3-methyl-ceph-3-em-4-carboxylic acid trichloroethyl ester, 7-(α-Phenoxycarbonyl-phenylacetamido)-3-methyl-ceph-3-em-4-carboxylic acid, 7-(α-Carboxy-propylacetamido)-3-methyl-ceph-3-em-4-carboxylic acid;

7-(α-Carboxy-propylacetamido)-3-methyl-ceph-3-em-4-carboxylic acid trichloroethyl ester, 7-(α-Carboxy-p-chlorophenylacetamido)-3-methyl-ceph-3-em-4-carboxylic acid, and 7-(α-Carboxy-o-bromophenylacetamido)-3-methyl-ceph-3-em-4-carboxylic acid.

According to the known methods, α-carboxyaryl-penicillanic acid and cephalosporanic acid derivatives are prepared generally by reacting a salt or an ester of 6-APA or 7-ADCA with an aryl-substituted malonic chloride containing an ester-forming group on one of the carboxyl groups.

When the ester-forming group attached to the α-carboxyl group is to be removed, this is done generally by hydrogenolysis or by mild basic hydrolysis (see U.S. Pat. No. 3,492,291).

According to the process disclosed in the Hungarian Pat. No. 161,609 first a dichloride of an aryl-substituted malonic acid is prepared, and the amino group of 6-APA or 7-ADCA is acylated selectively with this reagent under appropriately adjusted reaction conditions. The reaction product is thereafter subjected to aqueous hydrolysis to obtain the respective α-carboxy-penicillanic acid or α-carboxy-cephalosporanic acid derivatives.

According to the process disclosed in the U.S. Pat. No. 3,557,090 first an aryl-malonic acid dichloride is reacted with a tertiary base or is subjected to thermal decomposition to obtain an aryl-chlorocarbonyl-ketene reagent. Owing to the fact that in the subsequent acylation step both the acyl group and the ketene function of the reagent can act as an acylating agent, the obtained aryl-chlorocarbonyl-ketene compounds are subsequently reacted with an alcohol to form the respective monoesters. This reaction should be performed at very low temperatures (e.g. at −70° C.) in order to avoid the formation of diesters. The thus obtained monoesters are used as acylating agents in the preparation of the α-carboxy-penicillanic or α-cephalosporanic compounds.

The disadvantages of these known processes can be summarized as follows:

(a) When the acylation is performed with a chloride of an aryl-substituted malonic acid hemiester, the obtained product should always be subjected to a subsequent hydrolysis step. This hydrolysis decreases the yield, and can lead to the formation of undesired decomposition products, particularly when the very sensitive penicillanic acid derivatives are involved.

(b) The hydrolysis step cannot be avoided when a hemiester formed from a chlorocarbonyl-ketene is used as the reactant. Thus the disadvantages listed under point (a) also hold for this reaction.

(c) When the coupling is carried out using aryl-malonic dichlorides, several undesired by-products are formed. A further problem arises from the fact that the aryl-malonic dichlorides are very susceptible to polymerization; thus they cannot be prepared in pure state or stored on an industrial scale.

(d) A common disadvantage of all the known processes listed above is that the acylating agents utilized are labile compounds liable to decomposition, thus they cannot be stored, cannot be purified from the accompanying impurities, and must be processed immediately.

Now it has been found, unexpectedly, that the malonic acid esters of the formula (III) can be used very advantageously in the acylation of amine compounds, and when reacted with the amines in the presence of a tertiary base, they form the respective amides with excellent yields and in a high degree of purity.

The reaction can be controlled by varying the amount of the tertiary base introduced. Thus if a di-pentachlorophenyl aryl-malonate is used as acylating agent, and only one mole of a tertiary base is added to the mixture calculated for one mole of the acylating agent, the pentachlorophenyl ester of the respective α-carboxy derivative is obtained. If, however, a further mole of a tertiary base is introduced into the reaction mixture, a ketene derivative of the respective aryl-malonic amide is formed in the reaction mixture which, upon treatment with dilute sodium carbonate solution, yields the appropriate sodium carboxylate compound.

Thus, if the esters of the respective α-carboxy-6-APA or -7-ADCA derivatives are to be prepared, the malonic acid esters of the formula (III) or (IV), preferably the corresponding pentachlorophenyl esters prepared from various malonic acid hemiesters, are reacted with the appropriate amines in the presence of one molar equivalent of a tertiary base.

The reaction proceeds within a temperature range of 0° C. to 300° C., and the α-carboxy-penicillanic acid or cephalosporanic acid derivatives, or the esters thereof are obtained with excellent yields and in a high degree of purity.

If a di-pentachlorophenyl aryl-malonate is used as acylating agent and the reaction is carried out in the presence of one molar equivalent of a tertiary base, the pentachlorophenyl ester of the obtained α-carboxy-phenyl-penicillanic acid or cephalosporanic acid can be isolated.

The acylating agents used in accordance with the invention are novel compounds which can be prepared with good yields and in a high purity grade from the appropriate arylmalonic dichlorides. These compounds need not be purified by distillation, do not decompose during storage, and can be used at any time for the in situ formation of the respective α-carboxyaryl-ketenes.

The reaction according to the invention proceeds under mild conditions, thus no destruction of the sensitive 6-APA or 7-ADCA skeleton occurs.

The reaction proceeds very quickly, generally within a period of some minutes to one or two hours.

As a reaction medium we prefer an organic solvent. Particularly preferred solvents are the halogenated hydrocarbons, such as methylene chloride, chloroform, dichloroethane, etc., but other organic solvents, such as benzene, dioxane, ether, and tetrahydrofuran, can be used as well.

As the tertiary base we can use a tertiary lower alkylamine, such as triethylamine or an aromatic amine, such as pyridine or an N,N-dialkyl-aniline.

The reaction proceeds very quickly, since the ketene formed in situ reacts immediately with the amine compound.

According to a preferred method of the invention an ester of the formula (IV)

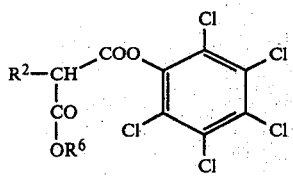

is used as acylating agent, wherein
$R^6$ is
(i) an aromatic group, preferably phenyl group, having a halogen, nitro, alkyl, alkoxy, acyl, carbamoyl or dialkylamino substituent,
(ii) a $C_{3-7}$ cycloalkyl group (such as cyclohexyl or cyclopentyl) having optionally a halogen or an alkyl substituent, or being optionally condensed with an aryl group (such as indanyl), or
(iii) unsubstituted benzyl or benzyl having a halogen, alkyl, alkoxy, acyl, nitro or dialkylamino substituent.

The method of the invention can be used to a great advantage for the economic plant-scale synthesis of 7-(-carboxy-phenylacetamino)-3-methyl-cephalosporanic acid or α-carboxy-benzylpenicillin. In this event the acylation is performed in the presence of at least 2 molar equivalent (preferably about 3 molar equivalents) of a tertiary base calculated for the amount of the acylating agent.

When an α-(halogenated-phenoxy)-carbonyl-benzylpenicillin, such as α-(pentachlorophenoxy)-carbonyl-benzylpenicillin or -benzyloxycarbonyl-benzylpenicillin, 7-(α-[benzyloxycarbonyl]-phenylacetamido)-3-methyl-cephalosporanic acid or a 7-(α-[halogenated phenoxycarbonyl]-phenylacetamido)-3-methyl-cephalosporanic acid, such as 7-(α-[pentachlorophenoxycarbonyl]-phenylacetamido)-3-methyl-cephalosporanic acid is to be prepared, in accordance with the invention, a maximum 1.5 moles, preferably 1 mole of a tertiary base is used per 1 mole of the acylating agent.

As acylating agent e.g. a di-pentachlorophenyl ester of a phenyl-substituted malonic acid can be used, but a 3-thienyl, 3-furyl, 3-methoxyphenyl, 4-methoxyphenyl, 3-pyridyl, o-chlorophenyl, o-bromophenyl, p-chlorophenyl -or o-butoxyphenyl-compound can be used as well. One may, however, also use a mixed malonic acid ester, wherein only one of the esterifying groups is pentachlorophenyl.

Thus the acylation can be carried out preferably with phenylmalonic acid pentachlorophenylester benzylester, phenylmalonic acid 5-indanylester pentachlorophenylester, phenylmalonic acid pentachlorophenylester ethylester, phenylmalonic acid pentachlorophenylester allylester, phenylmalonic acid pentachlorphenylester acetoxymethylester, phenylmalonic acid pentachlorphenylester 2,2,2-trichloroethylester, phenylmalonic acid pentachlorophenylester p-nitrobenzylester, phenylmalonic acid pentachlorophenylester phenacylester, phenylmalonic acid pentachlorophenylester p-nitro-phenacylester, etc.

One may also use as acylating agent the 3-substituted derivatives of the above mixed esters, wherein the substituent attached to position 3 is a thienyl, furyl, alkoxyphenyl, or pyridyl group.

The reaction conditions are selected preferably so that the acylation proceeds at a temperature from $-70°$ C. to $+60°$ C., particularly $-10°$ C. to $+30°$ C.

The $R^4$ protecting group can be split off by methods well known in the art; the actual method used depends on the nature of the protecting group and the ring system.

If a penicillanic acid derivative is to be prepared, preferably a trialkylsilyl or a trialkylamino group is used as a protecting group. These groups can be removed by hydrolysis or, if a salt is to be prepared, by adjusting the pH of the mixture to an appropriate value.

Thus, for example, a trialkylamino protecting group can be used to great advantage in the preparation of carbenicyllin. This group can be split off in a mild alkaline medium, preferably in the presence of a phosphate buffer. The new compounds of the formulae (V), (VI) and (VII), prepared in accordance with the invention

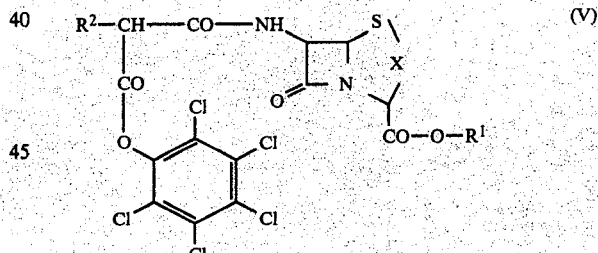

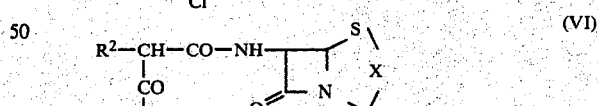

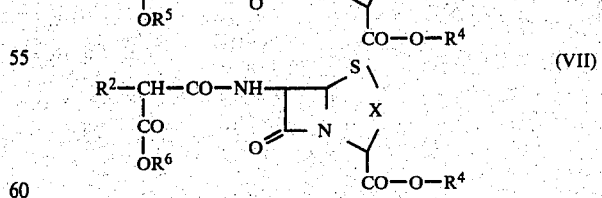

can be used to great advantage as starting substances in the preparation of novel penicillanic acid or cephalosporanic acid derivatives, since the reactive α-carboxylate group of these compounds reacts very easily with a wide variety of compounds, such as amines, etc. If desired, the compounds of the formula (I) can be converted into their alkali metal or alkaline earth metal salts, such as into the respective potassium, sodium or calcium salts.

The new malonic esters used as acylating agents in accordance with the invention can be prepared by methods used for the esterification of dicarboxylic acids (see e.g. French patent specification No. 2,038,933).

If a compound of the formula $R^3$ —OH is added instead of water to the compounds having the formula (V), the respective ester derivatives are obtained.

In an ester derivative of 7-ADCA, such as a trichloroethyl ester is acylated to obtain a mixed ester, the ester group attached to the dihydrothiazine ring can be split off selectively, e.g. by hydrogenolysis.

Thus, e.g. a zinc/hydrochloric acid mixture can be used for the selective removal of the trichloroethyl group.

According to the process of the invention preferably such compounds are used as starting substances which lead to the formation of particularly effective end-products.

The process according to the invention can be interrupted at any synthesis step, or can be performed starting from any intermediate obtained in a previous operation. Furthermore, the starting substances can also be formed directly in the reaction medium.

Depending on the reaction conditions utilized, the end-products are obtained either as free acids or in the form of their salts. The salts can be converted into the free acids by methods well known in the art. Alternately, the free acids can be converted into their salts by reacting them with a base, particularly with one containing a pharmaceutically acceptable cation. These compounds can be used in therapy in the form of pharmaceutical compositions.

The invention is elucidated in detail by the aid of the following non-limiting examples.

The thin layer chromatographical examinations were performed on Kieselgel G Stahl (prepared by the firm E. Merck, Darmstadt), using o-toluidine/potassium iodide as developing agent. The following solvent systems were utilized in the tlc examinations: system 13: a 20:10 mixture of benzene and ethyl acetate, and system ⅓ 9: a 120:20:2:1 mixture of ethyl acetate, pyridine, glacial acetic acid and water.

The structure of the compounds were confirmed by IR and NMR spectroscopy as well as by elementary analysis. The degree of purity was checked by the conventional iodometric and acidimetric procedure.

Wherever the term "alkyl" appears herein and the number of carbons is unspecified, the "alkyl" contains 1 to 6 carbon atoms. Wherever the term "alkoxy" appears herein and the number of carbons is unspecified, the "alkoxy" contains 1 to 6 carbon atoms. Wherever the term "acyl" appears in the specification without further definition, the "acyl" is a $C_1$ to $C_6$ alkanoic group or benzoyl. Wherever the term "aryl" appears anywhere in the specification without further definition, the "aryl" is phenyl, 1-naphthyl, 2-naphthyl or 5-indanyl. "Cycloalkyl" has 3 to 8 carbon atoms.

EXAMPLE 1

6-(α-Carboxy-phenylacetamido)-2,2-dimethyl-penam-3-carboxylic acid 56 ml. (0.4 moles) or triethylamine are added to a suspension of 42 g. (10.2 moles) of 6-ABA in 600 ml. of methylene chloride. The obtained solution is cooled to 0° C., and 136 g. (0.2 moles) of phenylmalonic acid di-pentachlorophenylester are added to the solution at such a rate that the temperature should not rise above +5° C. Thereafter 28 ml. (0.2 moles) of triethylamine are added to the mixture, upon which the phenylmalonic acid di-pentachlorophenylester immediately dissolves. The mixture is stirred for 30 minutes, then 200 ml. of a 8% aqueous sodium hydrocarbonate solution is added. The pH of the mixture is adjusted to 7, and the methylenechloride phase is separated. The aqueous phase is covered with 200 ml. of ethyl acetate, and is acidified to pH=2 with 10% aqueous phosphoric acid.

The ethyl acetate phase is separated washed with 3×100 ml. of water, dried over magnesium sulfate, and diluted with 200 ml. of acetone. Thereafter sodium diethylacetate is added to the mixture in order to precipitate the product as its sodium salt. The separated precipitate is filtered off, washed with 200 ml. of acetone, and dried. 67 g. (80%) of sodium 6-(α-carboxy-phenylacetamido)-2,2-dimethyl-penam-3-carboxylate are obtained purity grade: 100% (determined by iodometry).

EXAMPLE 2

6-(α-Pentachlorophenoxycarbonyl-phenylacetamido)-2,2-dimethyl-penam-3-carboxylic acid 5.6 ml. (10.04 moles) of triethylamine are added to a suspension of 4.2 g. (0.02 moles) of 6-APA in 60 ml. of methylene chloride. The mixture is stirred to obtain a clear solution, and then 13 g. (0.02 moles) of phenylmalonic acid di-pentachlorophenyl ester are added. The mixture is stirred at room temperature for 2 hours, and thereafter the obtained clear solution is evaporated in vacuo. The residue is taken up in 60 ml. of ethyl acetate. The solution is cooled to 0° C., and neutralized to pH=7 with 100 ml. of 5% aqueous sodium bi-carbonate solution. The organic phase is separated. The aqueous phase is covered with 100 ml. of ethyl acetate, and it is acidified to pH=3 with 2 n aqueous hydrochloric acid. The phases are separated from each other. The ethyl acetate solution is washed with 3×30 ml. of ice water, dried, and the solvent is evaporated. 8.5 g. (64%) of 6-(α-pentachlorophenoxycarbonyl)-benzylpenicillin are obtained as a yellowish-white, solid foam. Purity grade: 90% (determined by titrimetry).

EXAMPLE 3

6-(α-Carboxy-phenylacetamido)-2,2-dimethyl-penam-3-carboxylic acid 12.5 g. (0.02 moles) of 6-(α-pentachlorophenoxycarbonyl-phenylacetamido)-2,2-dimethyl-penam-3-carboxylic acid, prepared as described in Example 2, are suspended in 120 ml. of methylene chloride. The suspension is cooled to 0° C., 2.8 ml. (0.02 mole) of triethylamine are added, and the mixture is stirred at room temperature for 30 minutes. Thereafter the reaction mixture is decomposed with 8% aqueous sodium bi-carbonate solution.

Thereafter one proceeds as described in Example 1 to obtain 5.7 g. (70%) of 6-(α-carboxy-phenylacetamido)-2,2-dimethyl-penam-3-carboxylic acid disodium salt.

EXAMPLE 4

6-(α-Benzyloxycarbonyl-phenylacetamido)-2,2-dimethyl-phenam-3-carboxylic acid 2.8 ml. (0.02 moles) of triethylamine are added to a suspension of 2.1 g. (0.01 moles) of 6-APA in 30 ml. of methylene chloride, and 5.16 g (0.01 moles) of phenylmalonic acid pentachlorophenylester benzylester are added to the obtained solution. The reaction mixture is stirred at room temperature for 2 hours, thereafter it is decomposed with 8% aqueous sodium bi-carbonate solution. The mixture is processed as described above to obtain 3.5 g. (75%) of 6-(α-benzyloxycarbonyl-phenylacetamido)-2,2-dimethyl-penam-3-carboxylic acid as a yellowish, amorphous powder. $R_f$=0.7 (in System ½ 9).

EXAMPLE 5

6-(α-Carboxy-phenylacetamido)-2,2-dimethyl-penam-3-carboxylic acid

The aqueous-alkaline mixture obtained in Example 4 after the decomposition step is hydrogenated in the presence of palladium-on-carbon catalyst. The catalyst is filtered off, the filtrate is covered with 50 ml. of ethyl acetate, and the aqueous phase is acidified to pH=2 with 2 n aqueous hydrochloric acid. The ethylacetate phase is washed with water, dried, diluted with 50 ml. of acetone, and the 6-(α-carboxyphenylacetamido)-2,2-dimethyl-penam-3-carboxylic acid disodium salt is precipitated with sodium diethylacetate. The separated substance is filtered off and washed with acetone. 2.2 g (50%) of the aimed substance are obtained.

EXAMPLE 6

6-(α-[5-Indanyloxy-carbonyl]-phenylacetamido)-2,2-dimethyl-penam-3-carboxylic acid sodium salt 56 ml. (0.4 moles) of triethylamine are added to a suspension of 42 g. (0.2 moles) of 6-APA in 600 ml. of methylene chloride.

The obtained solution is cooled to 10° C., and 43.0 g (50 ml., 0.4 moles) of trimethyl-chlorosilane are added. The mixture is maintained at 35° C. for 60 minutes, thereafter it is cooled to 0° C., and 108. 3 g. (0.2 moles) of phenylmalonic acid pentachlorophenylester 5-indanylester are added. Subsequently 28 ml. (0.02 moles) of triethylamine are added dropwise to the mixture and the mixture is stirred at 0° C. for 3 hours. Thereafter the pH of the mixture is adjusted to 7 with 200 ml. of 8% aqueous sodium bi-carbonate solution.

The aqueous phase is separated, washed with ethyl acetate thereafter it is covered with 200 ml. of ethyl acetate, and acidified to pH=2 with 2 n aqueous hydrochloric acid. The ethyl acetate phase is separated, washed with water, dried over magnesium sulfate, and neutralized with sodium 2-ethylhexanoate. The solvent is evaporated, and the residue is triturated with diisopropyl ether. 80 g. (75%) of 6-(α-[5-indaniloxy-carboxy]-phenylacetamido)-2,2-dimethyl-penam-3-carboxylic acid sodium salt are obtained; m.p.: 220°–222° C. IR absorption bands: 1790 cm$^{-1}$ (lactam), 1750 cm$^{-1}$ (ester). $R_f$=0.75 (in System ½ 9).

EXAMPLE 7

6-(α-[5-Indanyloxy-carbonyl]-phenylacetamido)-2,2-dimethyl-penam-3-carboxylic acid triethylammonium salt 12.88 ml. (0.092 moles) of triethylamine are added to a suspension of 9.66 g (0.046 moles) of 6-APA in 150 ml. of dichloromethane, and the mixture is stirred at room temperature until a solution is obtained. The solution is cooled to 0° C., and 25 g. (0.046 moles) of phenyl-malonic acid pentachlorophenylester 5-indanylester are added to it at such a rate that the temperature of the mixture always remains below "5° C. The mixture is stirred at 0° C. for one hour, and thereafter the solvent is evaporated in vacuo. The residue is admixed with 100 ml. of ethyl acetate, whereupon 26 g. (98%) of 6-(α-[5-indanyloxy-carbonyl]-phenylacetamido)-2,2-dimethyl-penam-3-carboxylic acid triethylammonium salt separate in the form of a crystalline substance. M.p.: 153°–155° C.

Analysis: Calculated: C: 64.4% H: 7.04% N: 7.04%. Found: C: 6416% H: 7.24% N: 708%.

Purity grade: 99% (determined by iodometry).

IR absorption bands: 1780 cm$^{-1}$ (lactam, ester).

$R_f$=0.7 (in System ½ 9).

EXAMPLE 8

6-(α-[2,4-Dimethylphenoxycarbonyl]-phenylacetamido)-2,2-dimethyl-penam-3-carboxylic acid triethylammonium salt 4.2 ml. (0.03 moles) of triethylamine are added to a suspension of 3.24 g. (0.015 moles) of 6-APA in 60 ml. of dichloromethane, and the mixture is stirred at room temperature until a clear solution is obtained. The solution is cooled to 0° C., and 8 g. (0.015 moles) of phenyl-malonic acid 2,4-dimethyl phenylester pentachlorophenylester are added. The mixture is stirred at 0° C. for one hour, thereafter the solvent is evaporated, and the residue is admixed with 30 ml. of ethyl acetate. 8.4 g. (95%) of 6-(α-[2,4-dimethylphenoxycarbonyl]-phenylacetamido)-2,2-dimethyl-penam-3-carboxylic acid triethylammonium salt separate in the form of a white, crystalline substance. M.p.: 160°–165° C.

Analysis: Calculated: C: 63.8% H: 7.19% N: 7.19%. Found: C: 62.47% H: 7.20% N: 7.19%.

Purity grade: 98% (determined by iodometry).

$R_f$=0.7 (in System ½ 9).

IR absorption bands: 1.90 cm$^{-1}$ (lactam), 1760 cm$^{-1}$ (ester).

EXAMPLE 9

6-(α-[3,4-Dimethylphenoxylcarbonyl]-phenylacetamido)-2,2-dimethyl-penam-3-carboxylic acid triethylammonium salt 3.6 ml. (0.026 moles) of triethylamine are added to a suspension of 2.8 g. (0.013 moles) of 6-APA in 50 ml. of dichloromethane, and the mixture is stirred at room temperature until a clear solution is obtained. The solution is cooled to 0° C., 7 g. (0.013 moles) of phenylma-lonic acid 3,4-dimethylphenylester pentachlorophenylester are added, and the mixture is stirred at the same temperature for one hour. Thereafter the solvent is evaporated in vacuo, and the residue is admixed with 30 ml. of ethyl acetate. 7.5 g (95%) of 6-(α-[3,4-dimethyl-phenoxycarbonyl]-phenylacetamido)-2,2-dimethyl-penam-3-carboxylic acid triethylammonium salt separate in the form of a white, crystalline substance. M.p.: 155°–160° C.

Analysis: Calculated: C: 63.8% H: 7.19% N: 7.19%. Found: C: 63.54% H: 7.2% N: 7.24%.

Purity grade: 98%) determined by iodometry).

IR absorption bands: 1780 cm$^{-1}$ (lactam, ester).

$R_f$=0.7 (in System ½ 9).

EXAMPLE 10

6-(α-Phenoxycarbonyl-phenylacetamido)-2,2-dimethyl-penam-3-carboxylic acid triethylammonium salt 11.2 ml. (0.08 moles) or triethylamine are added to a suspension of 8.63 g (0.04 moles) of 6-APA in 120 ml. of methylene chloride. The obtained solution is cooled to 0° C. and 21 g. (0.04 moles) of phenylmalonic acid phenylester pentachlorophenylester are added in small portions so that the temperature of the mixture does not rise above +5° C. The mixture is stirred at 0° to +5° C. for one hour, thereafter the solvent is evaporated in vacuo, and the residue is triturated with 150 ml. of ethyl acetate. The separated crystalline substance is filtered off, and washed with ethyl acetate. 20 g. (90%) of 6-(α-phenoxycarbonyl-phenylacetamido)-2,2-dimethyl-penam-3-carboxylic acid triethylammonium salt are obtained. M.p.: 125°–130° C.

Analysis: Calculated: C: 63.0% H: 6.1% N: 7.6%. Found: C: 62.86% H: 6.20% N: 7.44%.

IR absorption band: 1790 cm$^{-1}$ (lactam, ester).

Purity degree: 99% (determined by iodometry).

$R_f$=0.7 (in System ½ 9).

EXAMPLE 11

6-(α-[5-Indanyloxycarbonyl]-phenylacetamido)-2,2-dimethyl-penam-3-carboxylic acid triethylammonium salt 2.8 ml. (0.02 moles) of triethylamine are added to a suspension of 2.17 g. (0.01 mole) of 6-APA in 50 ml. of methylene chloride. The obtained solution is cooled to −10° C. and 6.6 g (0.01 mole) of phenylmalonic acid di-pentachlorophenyl ester are added. The mixture is stirred at the same temperature for 30 minutes, and subsequently 1.4 ml. (0.01 mole) of triethylamine and 1.34 g. (0.01 mole) of 5-indanol are added. The temperature of the mixture rises to 0° to +5° C. The mixture is stirred at this temperature for one hours, then the solvent is evaporated, and the residue is triturated with di-isopropyl ether. 4.2 g. (70%) of 6-(α-[5-indanyloxycarbonyl]-phenylacetamido)-2,2-dimethyl-penam-3-carboxylic acid triethylammonium salt separate as a white powder. M.p.: 153°–155° C.

EXAMPLE 12

6-(α-[2,4-Dimethylphenoxycarbonyl]-phenylacetamido)-2,2-dimethyl-penam-3-carboxylic acid triethylammonium salt 2.8 ml. (0.02 moles) of triethylamine are added to a suspension of 2.17 g. (0.01 mole) of 6-APA in 50 ml. of methylene chloride. The obtained solution is cooled to −10° C., and 6.6 g. (0.01 mole) of phenylmalonic acid di-pentachlorophenyl ester are added. The mixture is stirred at the same temperature for 30 minutes, thereafter 1.4 ml. (0.1 mole) of triethylamine and 1.22 g. (0.01 mole) of 2,4-xylenol are added, whereupon the temperature of the mixture rises to 0° to +5° C. The mixture is stirred at this temperature for one hours, thereafter the solvent is evaporated, and the residue is triturated with diisopropyl ether. 4 g. (69%) of 6-(α-[2,4-dimethylphenoxycarbonyl]-phenyl-lacetamido)-2,2-dimethyl-penam-3-carboxylic acid triethylammonium salt are obtained; m.p.: 160°–165° C.

EXAMPLE 13

6-(α-Phenoxycarbonyl-phenylacetamido)-2,2-dimethyl-penam-3-carboxylic acid triethylammonium salt 2.8 ml. (0.02 moles) of triethylamine are added to a suspension of 2.17 g (0.01 mole) of 6-APA in 50 ml. of methylene chloride. The obtained solution is cooled to −10° C. and 6.6 g. (0.01 mole) of phenylmalonic acid di-pentachlorophenyl ester are added. The mixture is stirred at the same temperature for 30 minutes, thereafter 1.4 ml. (0.01 mole) of triethylamine and 1 g (0.011 moles) of phenol are added. The temperature is raised to 0° to +5° C., and the mixture is stirred for one hours. The solvent is evaporated, and the residue is treated with diisopropyl ether. 3.9 g. (70%) of 6-(α-phenoxycarbonyl-phenylacetamido)-2,2-dimethyl-penam-3-carboxylic acid triethylammonium salt are obtained.

EXAMPLE 14

6-(α-[5-Indanyloxycarbonyl]-phenylacetamido)-2,2-dimethyl-penam-3-carboxylic acid sodium salt A suspension of 25 g. (0.048 moles) of 6-(α-[5-indanyloxycarbonyl]-phenylacetamido)-2,2-dimethyl-penam-3-carboxylic acid triethylammonium salt in 150 ml. of ethyl acetate is cooled to 0° C., and the suspension is acidified with 2 n aqueous hydrochloric acid (13 ml.) to pH=2. The organic phase is separated and the aqueous-acidic phase is extracted with 2×20 ml. of ethyl acetate. The organic solutions are combined, washed with 3×30 ml. of saturated aqueous sodium chloride solution, dried over magnesium sulfate, filtered, and neutralized with a solution of 6.7 g. (0.048 moles) of sodium diethylacetate in 30 ml. of acetone. About 50% of the solvent is evaporated in vacuo. 100 ml. of diisopropyl ether are added to the concentrate, the mixture is cooled, and the obtained white, powdery substance is filtered off. 18 g. (80%) of 6-(α-[5-indanyloxycarbonyl]-phenylacetamido)-2,2-dimethyl-penam-3-carboxylic acid sodium salt are obtained; m.p.: 220°–222° C.

IR absorption bands: 1790 cm$^{-1}$ (lactam), 1750 cm$^{-1}$ (ester).

Analysis: Calculated: C: 60.3% H: 5.03% N: 5.40%. Found: C: 59.87% H: 5.2% N: 5.34%.

Purity degree: 99% (determined by iodometry).

$R_f$=0.75 (in System ½ 9).

EXAMPLE 15

6-(α-Phenoxycarbonyl-phenylacetamido)-2,2-dimethyl-penam-3-carboxylic acid sodium salt A suspension of 48 g. (0.09 moles) of 6-(α-phenoxycarbonyl-phenylacetamido)-2,2-dimethyl-penam-3-carboxylic acid triethylammonium salt in 250 ml. of ethyl acetate is cooled to 0° C., and acidified to pH=2.5 with 2 n aqueous hydrochloric acid. The organic phase is separated, washed with 2×30 ml. of saturated aqueous sodium chloride solution, filtered, and a solution of 12 g. (0.09 moles) of sodium diethylacetate in 50 ml. of acetone is added to the filtrate. The precipitated white powder is filtered off. 36 g. (85%) of 6-(α-phenoxycarbonyl-phenylacetamido)-2,2-dimethyl-penam-3-carboxylic acid sodium salt are obtained; m.p.: 233°–235° C.

IR absorption bands: 1790 cm$^{-1}$ (lactam), 1760 cm$^{-1}$ (ester).

$R_f$=0.75 (in System ½ 9).

EXAMPLE 16

6-(α-Phenoxycarbonyl-phenylacetamido)-2,2-dimethyl-penam-3-carboxylic acid sodium salt 56 ml. (0.4 moles) of triethylamine are added to a suspension of 42 g. (0.2 moles) of 6-APA in 600 ml. of methylene chloride. Subsequently 430 g. (0.4 moles, 50 ml.) of trimethyl chlorosilane are added to the obtained solution at 10° C., and the mixture is stirred for 60 minutes. Thereafter the mixture is heated to 35° C., 104 g. (0.2 moles) of phenylmalonic acid phenylester pentachlorophenyl ester are added, and subsequently 28 ml. (0.2 moles) of triethylamine are introduced dropwise into the mixture. The reaction mixture is stirred at room temperature for 3 hours, thereafter it is neutralized to pH=7 with 200 ml. of 8% aqueous sodium bi-carbonate solution.

The aqueous phase is separated and washed with ethyl acetate. Thereafter 200 ml. of ethyl acetate are layered into the aqueous phase, and the aqueous solution is acidified to pH=2 with 2 n aqueous hydrochloric acid. The ethyl acetate phase is separated, washed with water, dried over magnesium sulfate, filtrated, and sodium 2-ethyl-hexanoate is added to the filtrate. The separated substance is filtered off. 80 g. (73%) of 6-(α-phenoxycarbonyl-phenylacetanido)-2,2-dimethyl-penam-3-carboxylic acid sodium salt are obtained with a purity degree of 99% (determined by iodometry).

EXAMPLE 17

6-(α-Carboxy-2-[3-thienyl]-2,2-dimethyl-penam-3-carboxylic acid disodium salt 5.6 ml. (0.04 moles) of triethylamine are added to a suspension of 4.2 g (0.02 moles) of 6-APA in 60 ml. of methylene chloride. The obtained solution is cooled to 0° C., and 13.64 g. (0.02 moles) of 3-thienyl-malonic acid di-pentachlorophenyl ester are added at such a rate that the temperature of the mixture does not rise above +5° C. Thereafter 2.8 ml. (0.02 moles) of triethylamine are added to the mixture. The obtained clear solution is stirred for 30 minutes, and subsequently it is neutralized to pH=7 with 20 ml. of a 8% aqueous sodium bi-carbonate solution. The organic phase is separated. The aqueous phase is covered with ethyl acetate, and acidified to pH=2 with 10% aqueous phosphoric acid. The ethyl acetate phase is separated, washed thrice with water, dried over magnesium sulfate, filtered, and the filtrate is diluted with acetone. Thereafter sodium diethylacetate is added to the solution in order to precipitate the product. The separated precipitate is filtered off, washed with acetone, and dried. 6.7 g. (80% of 6-(α-carboxy-3-thienyl-acetamide)-2,2-dimethyl-penam-3-carboxylic acid disodium salt are obtained with a purity degree of 100% (determined by iodometry).

EXAMPLE 18

7-(α-Phenoxycarbonyl-phenylacetamido)-3-methyl-ceph-3-em-4-carboxylic acid 4.2 ml. (0.03 moles) of triethylamine are added to a suspension of 2.2 g. (0.01 mole) of 7-ADCA in 50 ml. of acetonitrile and 2 ml. of water. The obtained clear solution is cooled to 0° C., and 5.02 g. (0.01 mole) of phenyl-malonic acid phenylester pentachlorophenyl ester are added. The mixture is stirred at room temperature for 2 hours, and subsequently the acetonitrile is removed by evaporation. The residue is admixed with ethyl acetate and acidified with 2 n aqueous hydrochloric acid. The ethyl acetate phase is separated, dried and evaporated. The residue is triturated with diisopropyl ether to obtain 3.4 g. (75%) of 7-(α-phenoxycarbonyl-phenylacetamido)-3-methyl-ceph-3-em-4-carboxylic acid; m.p: 176°-178° C.

Analysis: Calculated: C: 61.0% H: 4.64% N: 6.18%. Found: C: 60.9% H: 4.50% N: 6.00%.

$R_f$=0.8 (in System ½ 9).

EXAMPLE 19

7-(α-[5-Indanyloxycarbonyl]-phenylacetamido)-3-methyl-ceph-3-em-carboxylic acid 4.2 g. (0.03 moles) of triethylamine are added to a suspension of 2.2 g. (0.01 mole) of 7-ADCA in 50 ml. of acetonitrile and 2 ml. of water. The obtained clear solution is cooled to 0° C., and 5.4 g. (0.01 mole) of phenyl-malonic acid 5-indanylester pentachlorophenylester are added. The mixture is stirred at room temperature for 2 hours. Thereafter the acetonitrile is evaporated, the residue is taken up in ethyl acetate, and the solution is acidified with 2 n aqueous hydrochloric acid. The ethyl acetate phase is separated, dried and evaporated. The residue is triturated with diisopropyl ether to obtain 3.8 g. (76%) 7-(α-[5-indanyloxycarbonyl]-phenylacetamido)-3-methyl-ceph-3-3m-4-carboxylic acid; m.p.: 168°-170° C.

Analysis: Calculated: C: 63.0% H: 5.4% N 5.4%. Found: C: 62.25% H: 5.25% N: 5.31%.

EXAMPLE 20

7-(α-Phenoxycarbonyl-phenylacetamido)-3-methyl-ceph-3-em-4-carboxylic acid triethylammonium salt 4.2 ml. (0.03 moles) of triethylamine are added to a suspension of 2.2 g. (0.01 mole) of 7-ADCA in 50 ml. of acetonitrile and 2 ml. of water. The obtained clear solution is cooled to −10° C., and 6.67 g. (0.01 mole) of phenylmalonic acid di-pentachlorophenyl ester are added at such a rate that the temperature of the mixture does not rise above −10° C. The phenylmalonic acid di-pentachlorophenyl ester dissolves in the mixture. The mixture is stirred at the same temperature for 30 minutes, thereafter a solution of 1 g. of phenol and 1.4 ml. of triethylamine in 10 ml. of acetonitrile is added dropwise. The mixture is warmed to 0° C. and stirred at this temperature for one hour. Thereafter the acetonitrile is evaporated, and the residue is triturated with diisopropyl ether. 4.2 g. (72%) of 7-(α-phenoxycarbonyl-phenylacetamido)-3-methyl-ceph-3-em-4-carboxylic acid triethylammonium salt are obtained as a yellowish-white, amorphous powder.

EXAMPLE 21

7-(α-Carboxy-3-thienyl-acetamido)-3-methyl-ceph-3-em-4-carboxylic acid 4.2 ml. (0.03 moles) of triethylamine are added to a suspension of 2.2 g. (0.01 mole) of 7-ADCA in 50 ml. of acetonitrile and 2 ml. of water. The obtained clear solution is cooled to 0° C. and 6.80 g. (0.01 mole) of 3-thienyl-malonic acid di-pentachlorophenyl ester are added at such a rate that the temperature of the mixture does not rise above +5° C. Thereafter 1.4 ml. (0.01 mole) of triethylamine are added, and the obtained clear solution is stirred for 30 minutes. The mixture is admixed with 10 ml. of a 8% aqueous sodium bi-carbonate solution, and the acetonitrile is evaporated in vacuo. The obtained aqueous residue is covered with 30 ml. of ethyl acetate, and the pH of the aqueous phase is adjusted to 2 with 2 n aqueous hydrochloric acid. The ethyl acetate phase is separated, washed with water, dried over magnesium sulfate, and evaporated in vacuo. The residue is triturated with ether. 3 g. (80%) of 7-(α-carboxy-3-thienyl-acetamido)-3-methyl-ceph-3-em-carboxylic acid are obtained with a purity degree of 99% (determined by acidimetry).

Analysis: Calculated: C: 46.9% H: 4.28% N: 7.5% S: 16.6%. Found: C: 45.9% H: 4.15% N: 7.4% S: 15.9%.

EXAMPLE 22

7-(α-[5-Indanyloxycarbonyl]-phenylacetamido)-3-methyl-ceph-3-em-4-carboxylic acid trichloroethyl ester 2.8 ml. (0.02 moles) of triethylamine are added to a suspension of 3.8 g. (0.01 mole) of 7-amino-3-methyl-ceph-3-em-4-carboxylic acid trichloroethylester hydrochloride in 30 ml. of methylene chloride. The separated triethylamine hydrochloride is filtered off, the filtrate is cooled to 0° C., and 5.05 g (0.01 mole) of phenylmalonic acid pentachlorophenylester 5-indanylester are added. The obtained clear solution is stirred at the same temperature for 30 minutes, and subsequently it is washed with 2 n aqueous hydrochloric acid. The solvent is evaporated, and the residue is admixed with absolute ethanol. 4.8 g (80%) of 7-(α-[5-indanylcarbonyl]-phenylacetamido)-3-methyl-ceph-3-em-4-carboxylic acid trichloroethyl ester are obtained. The white, crystalline substance melts at 135°–138° C.

Analysis: Calculated: C: 54.1% H: 3.86% N: 4.50% Cl: 16.9%. Found: C: 53.9% H: 3.50% N: 4.25% Cl: 15.5%.

$R_f = 0.7$ (in System 13).

EXAMPLE 23

7-(α-Benzyloxycarbonyl-phenylacetamido)-3-methyl-ceph-3-em-4-carboxylic acid 1.8 ml. of pyridine are added to a suspension of 2.17 g. (0.01 mole) of 7-ADCA in 40 ml. of acetonitrile and 2 ml. of water. The obtained solution is cooled to 0° C., 5.6 g. (0.01 mole) of phenylmalonic acid pentachlorophenylester benzylester are added, and the mixture is stirred for 4 hours. The acetontrile is evaporated, the residue is taken up in 50 ml. of ethyl acetate, and the ethyl acetate solution is admixed with saturated sodium bi-carbonate solution. The aqueous phase is washed with ethyl acetate, thereafter it is covered with 50 ml. of ethyl acetate, and acidified to pH=2 with 2 n aqueous hydrochloric acid. The ethyl acetate phase is separated, dried, and evaporated. 3.5 g. (75%) of 7-(α-benzyloxycarbonyl-phenylacetamido)-3-methyl-ceph-3-em-4-carboxylic acid are obtained with a purity degree of 95% (determined by titrimetry).

IR absorption bands: 1790 cm$^{-1}$ (lactone) 1760 cm$^{-1}$ (ester).

EXAMPLE 24

7-(α-Phenoxycarbonyl-phenylacetamido-3-methyl-ceph-3-em-4-carboxylic acid trichloroethyl ester 2.8 ml. (0.02 moles) of triethylamine are added to a suspension of 3.8 g. (0.01 mole) of 7-amino-3-methyl-ceph-3-em-4-carboxylic acid trichloroethyl ester hydrochloride in 30 ml. of methylene chloride. The separated triethylamine hydrochloride is filtered off, the filtrate is cooled to 0° C., and 5.02 g (0.01 mole) of phenylmalonic acid phenylester pentachlorophenyl ester are added. The obtained clear solution is stirred at the same temperature for 30 minutes, thereafter it is washed with 2 n aqueous hydrochloride acid and the solvent is evaporated. The residue is treated with absolute ethanol. 4.7 g. (80%) of 7-(α-phenoxycarbonyl-phenylacetamido)-3-methyl-ceph-3-em-4-carboxylic acid trichloroethyl ester are obtained. The white, crystalline substance melts at 120°–125° C.

$R_f = 0.7$ (in System 13).

Analysis: Calculated: C: 51.6% H: 3.44% N: 4.81% Cl: 18.1%. Found: C: 51.7% H: 3.30% N: 4.60% Cl: 18.5%.

EXAMPLE 25

7-(α-Carboxy-phenylacetamido)-3-methyl-ceph-3-em-4-carboxylic acid 4.2 ml. (0.03 moles) of triethylamine are added to a suspension of 2.17 g. (0.01 mole) of 7-ADCA in 20 ml. of acetontrile and 2 ml. of water. The obtained clear solution is cooled to 0° C., and 6.8 g. (0.01 mole) of phenylmalonic acid di-pentachlorophenyl ester are added. The solution is stirred at 0° C. for one hour, and thereafter the acetonitrile is evaporated in vacuo. The residue is taken up in ethyl acetate, and the solution is admixed with 50 ml. of aqueous sodium bi-carbonate solution. The aqueous phase is separated, washed with 20 ml. of ethyl acetate thereafter it is covered with 50 ml. of ethyl acetate, and acidified to pH=2 with 4 n aqueous hydrochloride acid. The ethyl acetate phase is separated, dried over magnesium sulfate, and evaporated in vacuo. The residue is triturated with a small amount of ether to obtain 3 g. (79%) of 7-(α-carboxy-phenyl-acetamido)-3-methyl-ceph-3-em-4-carboxylic acid. The white amorphous powder melts at 180°–181° C. Purity degree: 98% (determined by acidimetry).

EXAMPLE 26

7-(α-Pentachlorophenoxycarbonyl-phenylacetamido)-3-methyl-ceph-3-em-4-carboxylic acid trichloroethyl ester 18 ml. (0.2 moles) of pyridine are added to a suspension of 38 g. (0.1 mole) of 7-ADCA-trichloroethyl ester hydrochloride in 400 ml. of methylene chloride. The obtained clear solution is cooled to 0° C., and 68 g. (0.1 mole) of phenylmalonic acid di-pentachlorophenyl ester are added to small portions. The mixture is stirred at the same temperature for 4 hours, thereafter the separated precipitate is filtered off. 68 g. (90%) of 7-(α-pentachlorophenoxycarbonyl-phenylacetamido)-3-methyl-ceph-3-em-4-carboxylic acid trichloroethyl ester are obtained; m.p.: 202° C.

IR absorption bands: 1790 cm$^{-1}$ (lactam), 1745 cm$^{-1}$ (ester), 1360 and 1390 cm$^{-1}$ (pentachlorophenyl).

Analysis: Calculated: C: 39.8% H: 2.1% N: 3.70% Cl: 37.6%. Found: C: 39.74% H: 2.05% N: 3.52% Cl: 37.49%.

EXAMPLE 27

7-(α-Benzyloxycarbonyl-phenylacetamido)-3-methyl-ceph-3-em-4-carboxylic acid trichloroethyl ester 1.8 ml. (0.02 moles) of pyridine are added to a suspension of 3.8 g. (0.01 mole) of 7-ADCA-trichloroethyl ester hydrochloride in 30 ml. of methylene chloride. The obtained mixture is cooled to 0° C., and 5.16 g. (0.01 mole) of phenylmalonic acid benzylester pentachlorophenyl ester are added. The reaction mixture is stirred for 5 hours, thereafter the solvent is evaporated, and the residue is recrystallized from absolute ethanol. 4.8 g. of 7-(α-benzyloxycarbonyl-phenylacetamido)-3-methyl-ceph-3-em-4-carboxylic acid trichloroethyl ester are obtained; m.p.: 148°–150° C.

Analysis: Calculated: C: 52.45% H: 2.87% N: 4.70% Cl: 17.60%. Found: C: 51.90% H: 2.75% N: 4.90% Cl: 17.85%.

EXAMPLE 28

7-(α-Pentachlorophenoxycarbonyl-phenylacetamido)-3-methyl-ceph-3-em-4-carboxylic acid p-nitro-phenacylester 1.6 ml. (0.016 moles) of pyridine are added to a solution of 3.5 g. (0.008 moles) of 7-ADCA-p-nitro-phenacylester in 50 ml. of methylene chloride. The solution is cooled to 0° C. 5.4 g. (0.008 moles) of phenylmalonic acid di-pentachlorophenyl ester are added, and the mixture is stirred for 5 hours. The separated substance is filtered off. 5 g. (80%) of 7-(α-pentachlorophenoxycarbonyl-phenylacetamido)-3-methyl-ceph-3-em-4-carboxylic acid p-nitro-phenacylester are obtained; m.p.: 188°–190° C.

Analysis: Calculated: C: 47.60% H: 2.7% N: 5.4% Cl: 22.3%. Found: C: 47.94% H: 2.64% N: 5.30% Cl: 23.6%.

EXAMPLE 29

7-(α-Phenoxycarbonyl-phenylacetamido)-3-methyl-ceph-3-em-4-carboxylic acid trichloroethyl ester 2.8 ml. (0.02 moles) of triethylamine and 1 g. (0.01 mole) of phenol are added to a 0° C. suspension of 7.55 g. (0.01 mole) of 7-(α-pentachlorophenoxycarbonyl-phenylacetamido)-3-methyl-ceph-3-em-4-carboxylic acid trichloroethyl ester in 50 ml. of methylene chloride. The reaction mixture is stirred at 0° C. for 5 hours at room temperature for 1 hour, thereafter it is washed with 2 n aqueous hydrochloric acid. The solution is dried and evaporated. The residue is treated with absolute ethanol. 4.4 g. (75%) of 7-(α-phenoxycarbonyl-phenylacetamido)-3-methyl-ceph-3-em-4-carboxylic acid trichloroethyl ester are obtained; m.p. 120°–125° C., $R_f$=0.7 (in System 13).

EXAMPLE 30

7-(α-Phenoxycarbonyl-phenylacetamido)-3-methyl-ceph-3-em-4-carboxylic acid 1.4 ml. (0.01 mole) of triethylamine are added to a suspension of 1.9 g. (0.005 moles) of 7-ADCA-trichloroethyl ester hydrochloride in 50 ml. of methylene chloride. The mixture is cooled to 0° C., 2.5 g. (0.005 moles) of phenylmalonic acid phenylester pentachlorophenyl ester are added, and the mixture is stirred at the same temperature for one hour. Thereafter stirring is continued for 3 hours at room temperature. The reaction mixture is washed with 20 ml. of 2 n aqueous hydrochloric acid, thereafter 20 ml. of 2 n hydrochloric acid and 2 g. of activated zinc are added. The mixture is stirred at room temperature for 2 hours. The methylene chloride phase is separated, washed with water, and extracted with a saturated aqueous sodium bi-carbonate solution. The aqueous-alkaline solution is washed with ethyl acetate, thereafter it is covered with ethyl acetate, and acidified to pH=2 with 2 n aqueous hydrochloric acid. The ethyl acetate phase is separated and evaporated. The residue is triturated with diisopropyl ether to obtain 1.5 g. (66%) of 7-(α-phenoxycarbonyl-phenylacetamido)-3-methyl-ceph-3-em-4-carboxylic acid. The white, crystalline substance melts at 176°–178° C.

EXAMPLE 31

7-(α-Carboxy-propylacetamido)-3-methyl-ceph-3-em-4-carboxylic acid 5.6 ml. (0.04 moles) of triethylamine are added to a suspension of 2.2 g. (0.01 mole) of 7-ADCA in 50 ml. of acetonitrile and 2 ml. of water. The obtained clear solution is cooled to 0° C., and 6.24 g. (0.01 mole) of ethylmalonic acid di-pentachlorophenyl ester are added. The reaction mixture is stirred for 3 hours. The obtained clear solution is evaporated, and the residue is dissolved in ethyl acetate. The solution is washed with 2 n aqueous hydrochloric acid and water, dried, and evaporated. The residue is triturated with diisopropyl ether to obtain 2.2 g. (65%) of 7-(α-carboxy-propylacetamide)-3-methyl-ceph-3-em-4-carboxylic acid; m.p.: 178°–180° C.

Analysis: Calculated: C: 47.5% H: 5.1% N: 8.2%. Found: C: 46.9% H: 5.3% N: 8.5%.

EXAMPLE 32

7-(α-Carboxy-propylacetamido)-3-methyl-ceph-3-em-4-carboxylic acid trichloroethyl ester 4.2 ml. (0.03 moles) of triethylamine are added to a suspension of 3.8 g. (0.01 mole) of 7-ADCA trichloroethyl esterhydrochloride in 50 ml. of methylene chloride. The mixture is cooled to 0° C., and 6.24 g. (0.01 mole) of ethylmalonic acid di-pentachlorophenyl ester are added. The temperature of the mixture rises to +5° C., and after 30 minutes of stirring a clear solution is obtained. The mixture is stirred for 3 hours, thereafter it is washed with 2 n aqueous hydrochloric acid and water, dried and evaporated. The residue is treated with ether. 3.5 g. (77%) of 7-(α-carboxy-propylacetamido)-3-methyl-ceph-3-em-4-carboxylic acid trichloroethyl ester are obtained; m.p.: 155°–160° C.

Analysis: Calculated: C: 39.3% H: 3.7% N: 6.1% Cl: 22.9%. Found: C: 38.5% H: 3.5% N: 6.0% Cl: 22.0%.

EXAMPLE 33

7-(α-Carboxy-p-chlorophenylacetamido)-3-methyl-ceph-3-em-4-carboxylic acid 5.6 ml. (0.04 moles) of triethylamine are added to a suspension of 2.17 g. (0.01 mole) of 7-ADCA in 50 ml. of acetonitrile and 2 ml. of water. The obtained clear solution is cooled to 0° C. and 7.1 g. (0.01 mole) of p-chlorophenylmalonic acid di-pentachlorophenyl ester are added at such a rate that the temperature of the mixture does not rise above +5° C. The obtained clear solution is stirred for 30 minutes, thereafter the acetonitrile is evaporated. The residue is dissolved in 50 ml. of ethyl acetate, the solution is washed with 2×10 ml. of 2 n aqueous hydrochloric acid and subsequently with water, dried, and the solvent is evaporated. The residue is triturated with ether to obtain 3.3 g. (80%) of 7-(α-carboxy-p-chlorophenylacetamido)-3-methyl-ceph-3-em-4-carboxylic acid as a white, amorphous powder. Purity degree: 99% (determined by acidimetry).

Analysis: Calculated: C: 49.8% H: 3.66% N: 6.84% Cl: 3.55%. Found: C: 47.9% H: 3.43% N: 6.70% Cl: 8.30%.

EXAMPLE 34

7-(α-Carboxy-o-bromophenylacetamido)-3-methyl-ceph-3-em-4-carboxylic acid 5.6 ml. (0.04 moles) of triethylamine are added to a suspension of 2.17 g. (0.01 mole) of 7-ADCA in 50 ml. of acetonitrile and 2 ml. of water. The obtained solution is cooled to 0° C., and 7.5 g. of o-bromophenylmalonic acid di-pentachlorophenyl ester are added at such a rate that the temperature of the mixture does not rise above +5° C. The obtained clear solution is stirred for 30 minutes, thereafter the acetonitrile is evaporated. The residue is dissolved in 50 ml. of ethyl acetate. The ethyl acetate solution is washed with 2 n aqueous hydrochloric acid, dried, and the solvent is evaporated. The residue is triturated with ethyl ether to obtain 3.6 g. (80%) of 7-(α-carboxy-o-bromophenylacetamido)-3-methyl-ceph-3-em-4-carboxylic acid with a purity degree of 98% (determined by acidimetry).

Analysis: Calculated: C: 44.8% H: 3.29% N: 6.16% Br: 17.6%. Found: C: 43.9% H: 3.10% N: 6.00% Br: 17.05%.

EXAMPLE 35

6-(α-Carboxy-p-chlorophenylacetamido)-2,2-dimethyl-penam-3-carboxylic acid disodium salt 2.8 ml. (0.02 moles) of triethylamine are added to a suspension of 2.17 g (0.01 mole) of 6-APA in 50 ml. of methylene chloride. The obtained solution is cooled to 0° C., and 7.1 g. (0.01 mole) of p-chlorophenylmalonic acid di-pentachlorophenyl ester are added. The mixture is stirred at this temperature for one hour. The obtained clear solution is neutralized to pH=7 with saturated aqueous sodium hydrocarbonate solution. The aqueous alkaline phase is separated, washed with ethyl acetate, and freeze-dried. 3.85 g. (80%) of 6-(α-carboxy-p-chlorophenylacetamido)-2,2-dimethyl-penam-3-carboxylic acid disodium salt are obtained. Purity degree: 98.5% (determined by iodometry) or 97% (determined by acidimetry), respectively.

Analysis: Calculated: C: 44.8% H: 3.29% N: 6.15% Cl: 7.70%. Found: C: 43.5% H: 3.33% N: 6.25% Cl: 7.20%.

EXAMPLE 36

6-(α-Carboxy-o-bromophenylacetamido)-2,2-dimethyl-penam-3-carboxylic acid disodium salt 2.8 ml. (0.02 moles) of triethylamine are added to a suspension of 2.17 g. (0.01 mole) or 6-APA. The obtained solution is cooled to 0° C., and 7.5 g. (0.01 mole) of o-bromophenylmalonic acid di-pentachlorophenyl ester are added. The mixture is stirred at the same temperature for one hour. The obtained clear solution is extracted with saturated aqueous sodium bi-carbonate solution. The aqueous-alkaline solution is washed with ethyl acetate, and freeze-dried. 3.7 g. (75%) of 6-(α-carboxy-o-bromophenylacetamido)-2,2-dimethyl-penam-3-carboxylic acid disodium salt are obtained. Purity degree: 99.5% (determined by iodometry) or 98.5% (determined by acidimetry), respectively.

Analysis: Calculated: C: 40.8% H: 3.00% N: 5.60% Br: 16.0%. Found: C: 39.2% H: 2.98% N: 5.15% Br: 16.55%.

We claim:

1. A process for preparation of a compound of the formula

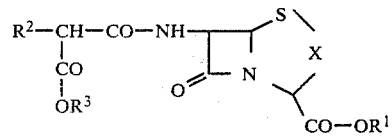

wherein
R$^1$ is nitrophenacyl;
R$^2$ is hydrogen, alkyl, alkenyl, alkyl having a conventional penicillin aryl heterocyclic substituent, or a conventional penicillin aryl, alkyl, cycloalkyl or aralkyl group;
R$^3$ is hydrogen, aryl, alkyl, cycloalkyl or aralkyl; and
X is a group selected from the formulae consisting of

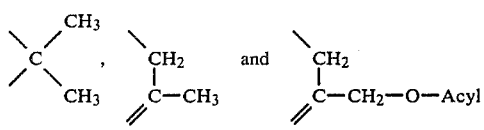

which comprises: reacting a compound of the formula

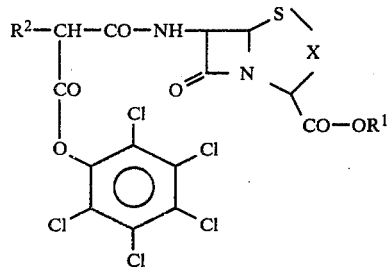

with a compound of the formula R$^5$—OH wherein R$^5$ is aryl, alkyl, cycloalkyl or aralkyl at a temperature of −10° C. to +30° C. for a period of up to 2 hours; and where R$^3$ is hydrogen, splitting off the substituent R$^5$.

2. A process for the preparation of a compound of the formula

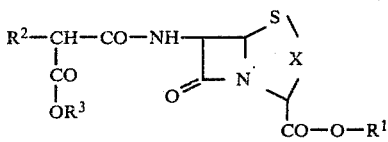

or a pharmaceutically acceptable salt thereof wherein
R$^1$ is nitrophenacyl;
R$^2$ is hydrogen, alkyl, alkenyl, alkyl having a conventional penicillin aryl heterocyclic substituent, or a conventional penicillin aryl, aralkyl, or heterocyclic group;
R$^3$ is hydrogen, aryl, alkyl, cycloalkyl or aralkyl; and
X is a group selected from the formulae consisting of

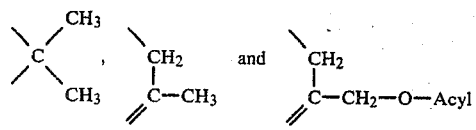

by acylating a compound of the formula

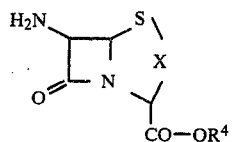

wherein
R⁴ is nitrophenacyl, in which the acylation is performed at a temperature of −10° C. to +30° C. for a period of up to two hours using an ester of the formula

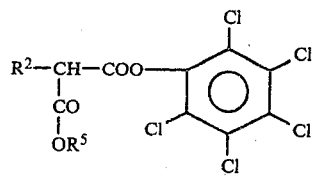

wherein
R⁵ is aryl, alkyl, cycloalkyl, or aralkyl; and wherein R³ is hydrogen, splitting off the substituent R⁵.

3. A process for the preparation of a compound of the formula

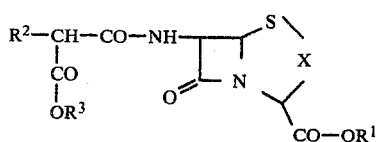

or a pharmaceutically acceptable salt thereof wherein
R¹ is nitrophenacyl;
R² is hydrogen, alkyl, alkenyl, alkyl having a conventional penicillin aryl heterocyclic substituent, or a conventional penicillin aryl, aralkyl, or heterocyclic group;
R³ is hydrogen; an aromatic group having a halogen, nitro, alkyl, alkoxy, acyl, carbamoyl or dialkylamino substituent; a C₃ to C₇ unsubstituted cycloalkyl or substituted by a halogen or an alkyl substituent, or being condensed with an aryl group; or a benzyl group or benzyl substituted by a halogen, alkyl, alkoxy, acyl, nitro or dialkylamino substituent; and
X is a group selected from the formulae consisting of

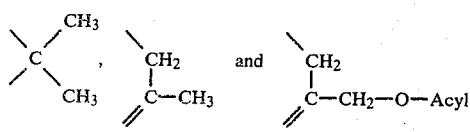

by acylating a compound of the formula

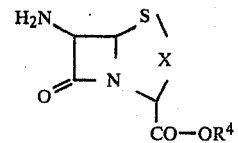

wherein
R⁴ is nitrophenacyl, in which the acylation is performed in the presence of a tertiary base selected from the group consisting of a trialkylamine, pyridine or N,N-dialkylaniline at a temperature of −10° C. to +30° C. using an ester of the formula

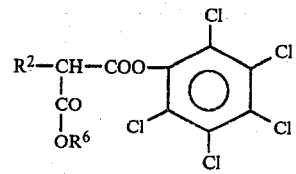

wherein
R⁶ is an aromatic group having a halogen, nitro, alkyl, alkoxy, acyl, carbamoyl or dialkylamino substituent; a C₃ to C₇ unsubstituted cycloalkyl or substituted by a halogen or an alkyl substituent, or being condensed with an aryl group; or a benzyl group or benzyl substituted by a halogen, alkyl, alkoxy, acyl, nitro, or dialkylamino substituent; and
wherein
R³ is hydrogen, splitting off the substituent R⁶.

4. The process defined in claim 2 or claim 3 wherein R³ is an aromatic group having a halogen substituent.

5. The process defined in claim 3 wherein R³ is pentachlorophenyl.

6. The process defined in claim 3 wherein R³ is indanyl.

7. A process for the preparation of a compound of the formula

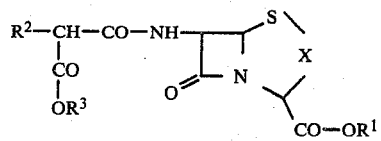

or a pharmaceutically acceptable salt thereof wherein
R¹ is hydrogen, trialkylamino, trialkylsilyl, trichloroethyl, acetoxymethyl, phenacyl, nitrophenacyl, phenyl or a benzyl group;
R² is hydrogen, alkyl, alkenyl, alkyl having a conventional penicillin aryl heterocyclic substituent, or a conventional penicillin aryl, aralkyl, or heterocyclic group;
R³ is hydrogen; an aromatic group having a halogen, nitro, alkyl, alkoxy, acyl, carbamoyl or dialkylamino substituent; a C₃ to C₇ unsubstituted cycloalkyl or substituted by a halogen or an alkyl substituent, or being condensed with an aryl group; or a benzyl group or benzyl substituted by a halogen, alkyl, alkoxy, acyl, nitro or dialkylamino substituent; and X is a group selected from the formulae consisting of

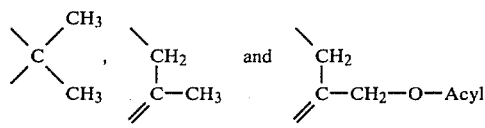

wherein the compound is selected from the group consisting of:
6-(α[5-indanyloxy-carbonyl]-phenylacetamido)-2,2-dimethyl-penam-3-carboxylic acid;
6-(α-[2,4-dimethylphenoxy-carbonyl]-phenylacetamido)-2,2-dimethyl-penam-3-carboxylic acid;
6-(α-[3,4-dimethylphenoxy-carbonyl]-phenylacetamido)-2,2-dimethyl-penam-3-carboxylic acid;
6-(α-phenoxy-carbonyl-phenylacetamido)-2,2-dimethyl-penam-3-carboxylic acid;
6-(α-carboxy-p-chlorophenylacetamido)-2,2-dimethyl-penam-3-carboxylic acid;
6-(α-carboxy-o-bromophenylacetamido)-2,2-dimethyl-penam-3-carboxylic acid;
7-(α-phenoxy-carbonyl-phenylacetamido)-3-methyl-ceph-3-em-4-carboxylic acid;
7-(α-[5-indanyloxy-carbonyl]-phenylacetamido)-3-methyl-ceph-3-em-4-carboxylic acid;
7-(α-phenoxy-carbonyl-phenylacetamido)-3-methyl-ceph-3-em-4-carboxylic acid triethylammonium salt;
7-(α-carboxy-3-thienyl-acetamido)-3-methyl-ceph-3-em-4-carboxylic acid;
7-(α-[5-indanyloxy-carbonyl]-phenylacetamido)-3-methyl-ceph-3-em-4-carboxylic acid trichloroethyl ester;
7-(α-phenoxy-carbonyl-phenylacetamido)-3-methyl-ceph-3-em-4-carboxylic acid trichloroethyl ester;
7-(α-pentachlorophenoxy-carbonyl-phenylacetamido)-3-methyl-ceph-3-em-4-carboxylic acid trichloroethyl ester;
7-(α-benzyloxy-carbonyl-phenylacetamido)-3-methyl-ceph-3-em-4-carboxylic acid trichloroethyl ester;
7-(α-pentachlorophenoxy-carbonyl-phenylacetamido)-3-methyl-ceph-3-em-4-carboxylic acid p-nitro-phenacylester;
7-(α-phenoxy-carbonyl-phenylacetamido)-3-methyl-ceph-3-em-4-carboxylic acid trichloroethyl ester;
7-(α-phenoxy-carbonyl-phenylacetamido)-3-methyl-ceph-3-em-4-carboxylic acid;
7-(α-carboxy-propylacetamido)-3-methyl-ceph-3-em-4-carboxylic acid;
7-(α-carboxy-propylacetamido)-3-methyl-ceph-3-em-4-carboxylic acid trichloroethyl ester;
7-(α-carboxy-p-chlorophenylacetamido)-3-methyl-ceph-3-em-4-carboxylic acid; and
7-(α-carboxy-o-bromophenylacetamido)-3-methyl-ceph-3-em-4-carboxylic acid, or a pharmaceutically acceptable salt thereof, which comprises the step of acylating a compound of the formula

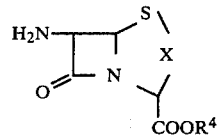

wherein
$R^4$ is an easily removable ester-forming group selected from the group which consists of trialkylamino, trialkylsilyl, trichloroethyl, acetoxymethyl, phenacyl, nitrophenacyl, phenyl and benzyl or a salt formed with an alkali metal or a trialkylamine in which the acylation is performed in the presence of a tertiary base selected from the group consisting of a trialkylamine, pyridine or N,N-dialkylaniline at a temperature of $-10°$ C. to $+30°$ C. using an ester of the formula

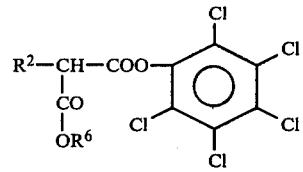

wherein
$R^6$ is an aromatic group having a halogen, nitro, alkyl, alkoxy, acyl, carbamoyl or dialkylamino substituent; a $C_3$ to $C_7$ unsubstituted cycloalkyl or substituted by a halogen or an alkyl substituent, or being condensed with an aryl group; or a benzyl group or benzyl substituted by a halogen, alkyl, alkoxy, acyl, nitro, or dialkylamino substituent; and
wherein
$R^1$ and $R^3$ are hydrogen, splitting off the substituents $R^4$ and $R^6$.

* * * * *